(12) United States Patent
Burch

(10) Patent No.: US 6,588,420 B1
(45) Date of Patent: *Jul. 8, 2003

(54) PEDIATRIC OXYGENATION DEVICE

(76) Inventor: John M. Burch, 2712 Kingston, Plano, TX (US) 75074

(*) Notice: Subject to any disclaimer, the term of this patent is extended or adjusted under 35 U.S.C. 154(b) by 0 days.

This patent is subject to a terminal disclaimer.

(21) Appl. No.: 08/926,113

(22) Filed: Sep. 9, 1997

Related U.S. Application Data

(63) Continuation of application No. 08/615,099, filed on Mar. 14, 1996, now Pat. No. 5,690,096.

(51) Int. Cl.⁷ .................. A61M 15/00; A61M 16/00; A62B 7/00
(52) U.S. Cl. .................. 128/200.24; 128/204.18
(58) Field of Search .................. 128/204.18, 200.24, 128/202.15, 207.18, 202.27, 205.26, 207.11; 46/202; 446/74

(56) References Cited

U.S. PATENT DOCUMENTS

| | | | |
|---|---|---|---|
| 2,628,803 A | 2/1953 | Krewson | 248/124 |
| 4,194,318 A | 3/1980 | Watanabe | 46/202 |
| D255,833 S | 7/1980 | Crandall | D24/1 |
| 4,377,161 A | 3/1983 | Whitt | 128/200.24 |
| 4,437,462 A * | 3/1984 | Piljay et al. | 128/207.11 |
| 4,520,809 A | 6/1985 | de Greef et al. | 128/200.24 |
| 4,593,688 A * | 6/1986 | Payton | 128/204.18 |
| 4,669,461 A | 6/1987 | Battaglia et al. | 128/202.15 |
| 4,982,874 A | 1/1991 | Pringle | 222/78 |
| 5,228,434 A | 7/1993 | Fishman | 128/203.12 |
| 5,230,648 A | 7/1993 | Kelly et al. | 446/74 |
| 5,370,111 A | 12/1994 | Reeder | 128/202.13 |
| 5,375,593 A | 12/1994 | Press | 128/207.18 |
| 5,389,037 A * | 2/1995 | Hale | 128/204.18 |
| 5,690,096 A * | 11/1997 | Burch | 128/204.18 |

* cited by examiner

Primary Examiner—Weilun Lo
Assistant Examiner—V. Srivastava
(74) Attorney, Agent, or Firm—Anderson, Levine & Lintel, LLP

(57) ABSTRACT

Oxygen is supplied to a pediatric patient through a plaything coupled to an oxygen source. Oxygen is dispensed through the plaything through one or more oxygen ports which allow the patient to interact with the plaything while maintaining a flow of oxygen near the mouth and nose of the patient for maximum oxygen transfer.

3 Claims, 6 Drawing Sheets

PEDIATRIC OXYGENATION DEVICE

RELATED APPLICATIONS

This application is a continuation of application Ser. No. 08/615,099, filed Mar. 14, 1996, and entitled "Pediatric Oxygenation Device", now U.S. Pat. No. 5,690,096.

BACKGROUND OF THE INVENTION

1. Technical Field

This invention relates in general to oxygenation devices and, more particularly, to a pediatric oxygenation device.

2. Description of the Prior Art

To an EMS (emergency medical service) provider, the most gratifying accomplishment is saving the life of a child or pediatric patient. In both adult and pediatric emergency situations, it is important to provide a high concentration of oxygen to the patient. The single most important element to the body, for both adults and children, is oxygen. For adult patients, oxygenation is accomplished by applying a mask over the nose and mouth of the patient. Oxygen from an oxygen tank is supplied to the mask through a tube, such that the patient breaths pure oxygen. Pediatric patients, however, can be significantly more difficult to oxygenate than adult patients.

With pediatric patients, early and efficient oxygenation is more critical than with adults. Smaller airways prevent children from moving as much oxygen as adults, as well as make them more susceptible for choking on foreign objects. Further, children have smaller lung volumes, fewer and smaller alveoli (which are more susceptible to collapse) and lower hemoglobin levels, and hence less oxygen carrying capacity, The inability to move sufficient quantities of oxygen can be critical when the patient is sick or injured.

Smaller blood volume in a child further increases the difficulty of reoxygenating a pediatric patient once he or she becomes hypoxic. Not only is there less blood volume, but there is proportionately less hemoglobin to carry oxygen. Therefore, once a child becomes low on oxygen, a significant period of time is necessary to return their oxygen state to a normal level.

With the metabolic rate of kids being twice that of adults, their normal rate of oxygen consumption is much greater. Considering that the pediatric patient in an emergency situation is typically traumatized by illness or injury, the metabolic rate increases even more, as does the patient's heart rate, causing an extreme demand for oxygen. Consequently, hypoxia occurs much quicker in children than it does in adults and it takes children longer to recover.

Unfortunately, administering oxygen to pediatric patients can be much more difficult than with adults. Children are easily intimidated by an emergency medical setting. Children are taught from an early age that strangers are bad and to stay away from strangers. So when strangers try to give aid to children, their apprehension is a very normal, conditioned response.

Additionally, some young children are unable to communicate and some older children do not have sufficient communication skills to communicate easily. Therefore, it is often difficult to determine their problem.

Because of a pediatric patient's intimidation and his or her inability to quickly and effectively communicate with the emergency medical personnel, the administration of oxygen can be extremely difficult. Oxygenation using a mask, as is done with adults, is difficult because the natural instinct of many children is to fight against anything being placed over their breathing passages. This is particularly true in the emergency medical situation where the mask and oxygenation equipment is very strange to children. Accordingly, it is likely that a child will struggle with EMS personnel if a mask is placed on or near their face. Therefore, EMS personnel often hold the mask in the general vicinity of the pediatric patient's face, but children will still turn away from the mask and become aggravated. Struggling increases the need for oxygen, while decreasing the ability to receive oxygen from the mask. As the child becomes more upset, the demand for oxygen increases and the patient's consumption of oxygen increases, causing the child to become more hypoxic, possibly to a degree greater than before oxygen was administered.

A number of devices have been designed to administer oxygen or other gases to infants in non-emergency settings using a bottle nipple or pacifier. Such devices are shown in U.S. Pat. No. 4,669,461 to Battaglia, U.S. Pat. No. 4,520,809 to de Greef and U.S. Pat. No. 5,375,593 to Press. These devices are not useful in emergency settings for a number of reasons. First, the attraction to a bottle nipple or pacifier is not universal, even in infants. Some infants, particularly breast fed infants, will turn away from a bottle nipple. Second, those infants who are attracted to a bottle nipple or a pacifier will want to put the object in their mouths and suck on the nipple, thereby eliminating the mouth as a source for receiving oxygen. Breathing oxygen solely through the nose can significantly decrease the volume of oxygen received by the patient. Third, a nipple is generally not attractive to older pediatric patients, who will resist, refuse, or have no interest in the nipple.

Therefore, there is a need in the industry for a device for administering oxygen to a pediatric patient in an emergency situation which efficiently supplies oxygen and calms the patient.

SUMMARY OF THE INVENTION

An oxygenation device is shaped as a plaything. A connector on the plaything couples to an oxygen source for supplying oxygen. At least one outlet is coupled to the connector, such that oxygen from said oxygen source is dispersed in the area of the plaything so that a patient holding the plaything will receive a high concentration of oxygen.

The present invention provides significant advantages over the prior art. First, it delivers oxygen to a pediatric patient without adding to stress. Second, it may actually reduce stress in the patient. Third, it can deliver oxygen over a wide area, allowing the patient to interact with the plaything in a natural manner while maintaining a direct flow of oxygen to the patient's mouth and nose regions. Fourth, the oxygenation device can be inexpensively made. Fifth, different designs can be used to appeal to a wide range of pediatric patients.

BRIEF DESCRIPTION OF THE DRAWINGS

For a more complete understanding of the present invention, and the advantages thereof, reference is now made to the following descriptions taken in conjunction with the accompanying drawings, in which:

FIG. 3 illustrates an oxygen port for the ear pieces of FIG. 2a;

FIGS. 4a–b illustrate front and side views, respectively of an oxygen port for the nose piece of FIG. 2a;

FIGS. 5a–b illustrate an oxygen port for the paw and belly pieces of FIG. 2a;

DETAILED DESCRIPTION OF THE PREFERRED EMBODIMENT

The present invention is best understood in relation to FIGS. 1–9 of the drawings, like numerals being used for like elements of the various drawings.

Figure 1:
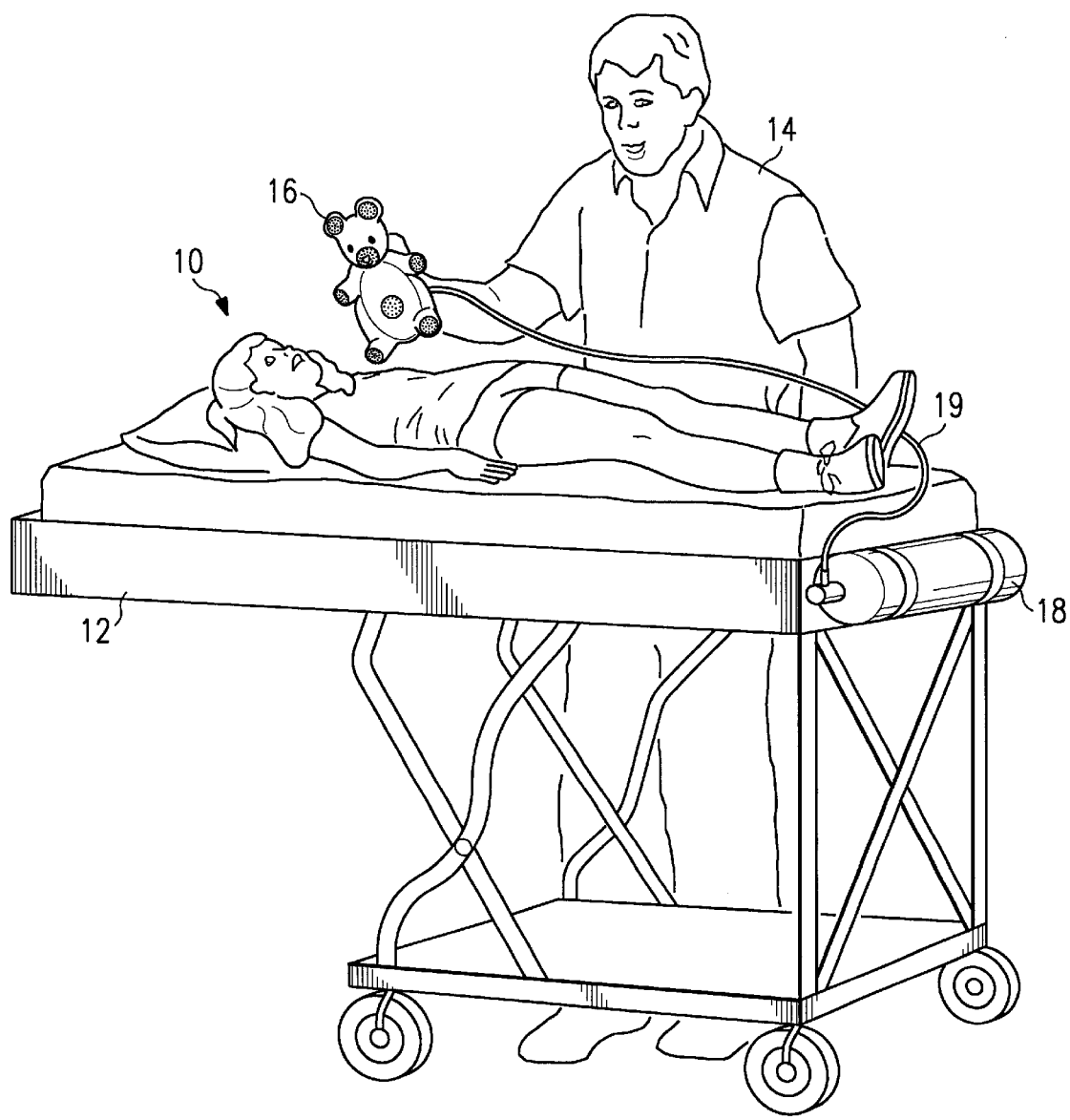
FIG. 1 illustrates a perspective view of an emergency scenario using a pediatric oxygenation device to supply oxygen to the patient.

FIG. 1 illustrates a view of an emergency medical situation wherein the present invention is used to supply oxygen to a pediatric patient. The patient 10 is shown on a bed 12 inside of an emergency vehicle, although the present invention would be suitable for use at the emergency scene or for emergency rooms in a hospital setting as well. An EMS caretaker 14 provides the patient 10 with a pediatric oxygenation device 16 which is shaped as a plaything, shown in greater detail below. The pediatric oxygenation device is coupled to an oxygen source 18, such as an oxygen tank, by main tubing 19. Oxygen tank 18 can be regulated to supply a desired flow of oxygen to the plaything.

When a child has a medical emergency, it is often the case that the cause can not be immediately determined. Some illnesses, such as croup, epiglottitis, asthma, anaphylaxis, pneumonia, bronchiolitis and foreign body obstruction, to name a few, can all negatively affect a pediatric patient's oxygenation. Croup and epiglottitis are impossible to differentiate in the pre-hospital setting. The most important rule is to calm the patient and supply supplemental oxygen. Upsetting the patient can cause the epiglottis to spasm, which can completely obstruct the patient's airway. Asthma is an illness which appears to be on the rise, especially with children. One of the most important aspects of treating asthma is supplemental oxygen, which helps prevent the child from becoming hypoxic.

Anaphylaxis is a severe, potentially fatal, allergic reaction. It seems more children, as well as adults, have allergies to more things than in the past. Again, supplemental oxygen is important in treating the reaction. Pneumonia and bronchiolitis are illnesses caused by a virus. Both affect the patient's lungs, which, in turn, affect the oxygenation process by decreasing the patient's ability to properly oxygenate the blood. Once again, supplemental oxygen and a calm environment are important factors in treating the patient.

Foreign body obstructions are common in pediatric patients, much more common than in adults, due to curiosity and small airways. Curiosity causes small children to put objects in their mouths. Small airways lead to easier obstruction by an object. When a child is choking and the object cannot be removed, supplemental oxygen is of eminent importance. Further, a choking child is likely to be in a frantic state and restoring calm to the child is very important.

Accordingly, the EMS personnel 14 will attempt to administer oxygen to a pediatric patient immediately. Unfortunately, a mask, even if held away from the child, will often cause the child to struggle.

In operation, the oxygenation device 16 receives oxygen from the oxygen source 18 and distributes the oxygen from one or more outlets associated with the plaything 18. Accordingly, a high concentration of oxygen is located in the area of the plaything.

Because the oxygenation device is shaped like a plaything, the pediatric patient 10 is likely to hug or otherwise hold the oxygenation device 16 near his or her face. If the patient's natural instincts do not cause the patient 10 to hold the oxygenation device 16 near his or her face, such positioning of the plaything can be easily accomplished through encouragement by the EMS caretaker 14 or by parents. Not only is the plaything not a source of anxiety to the patient 10, it has the reverse effect, calming the patient 10 by focusing the patient's attention on a friendly object, rather than the unfamiliar equipment and personnel found in an emergency scene.

Accordingly, the oxygenation device 16 provides two services. First, it provides an area of high oxygen concentration around the face of the patient 10. Second, it calms the patient 10 to reduce the patient's oxygen consumption. Thus, the oxygenation device 16 increases the speed at which the patient is re-oxygenated.

Figure 2A:
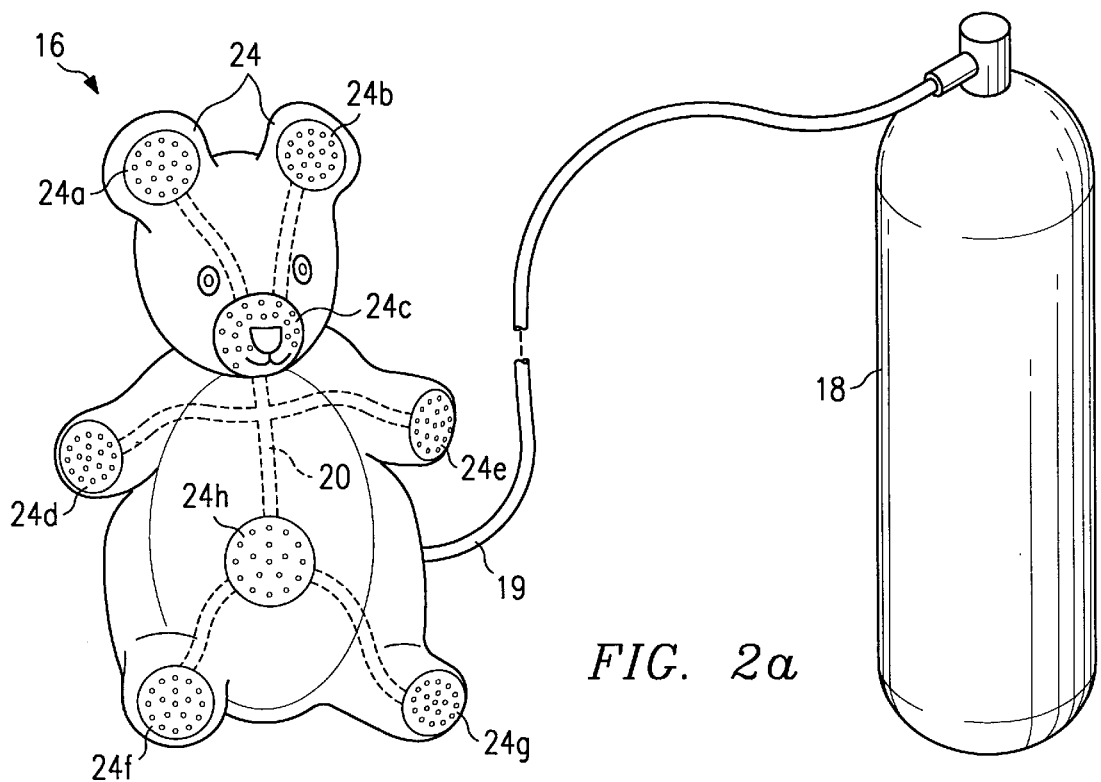
FIG. 2a illustrates a perspective view of a first embodiment of the pediatric oxygenation device.

FIG. 2a illustrates a perspective view of a first embodiment of the oxygenation device 16 coupled to an oxygen source 18. In this embodiment, oxygenation device 16 is shaped like a teddy bear, which is a familiar and friendly object to children of both sexes. The oxygenation device 16 has internal tubing 20 which is coupled to the oxygen source 18 by a fitting 22 (shown in greater detail in connection with FIG. 2b). In the preferred embodiment, the tubing 20 has a plurality of branches to multiple oxygen ports 24. In the illustrated embodiment, oxygen ports 24 are disposed at the bear's ears (individually referenced as oxygen ports 24a–b), muzzle (individually referenced as outlet site 24c), paws (individually referenced as oxygen ports 24d–g) and belly (individually referenced as outlet site 24h).

Many configurations and designs can be used to implement the invention, some of which are shown below. Accordingly, the dimensions provided herein may be varied as necessary to accomplish the desired result of supplying oxygen to the area in front of the pediatric patient's face.

The oxygenation device 16 should be about nine inches tall, when in a sitting position as shown in FIG. 2a. The particular dimensions of the bear's features would be proportional to this height. The overall goal is to dimension the oxygenation device 16 to be large enough to provide a broad area of oxygenation, while being a size which can easily be held by the patient. In this regard, it may be desirable to design playthings in different sizes for children of different sizes.

The exterior body of the plaything should be made of a material which is pleasing to hold. This material could be a short fur-like material, as of the type used to make stuffed animals, a velvet or velour material, or even a smooth plastic, such as the type used to make baby dolls. The goal is to have a oxygenation device 16 which the child will not mind having around his or her face. Hypoallergenic or completely sterile bears could also be made using materials known in the medical arts.

In the embodiment shown in FIG. 2a, the main tubing 19 from the oxygen source 18 is coupled to the tail of the teddy bear, although the connection could be made in a variety of places. The main consideration involving placement of the main tubing connector on the plaything is that the tubing should not interfere with the holding of the oxygenation device 16 near the patient's face, nor should it be located in a position where such holding may crimp the main tubing and restrict oxygen flow into the oxygenation device 16.

Figure 2B:
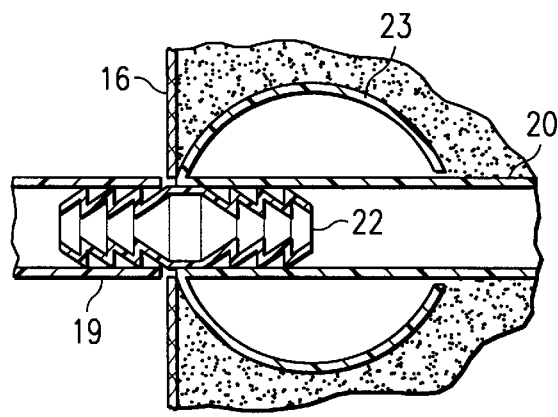
FIG. 2b illustrates a cross-sectional view of the connection of the pediatric oxygenation device to the oxygen source.

FIG. 2b illustrates a cross sectional view of the connection between the oxygenation device 16 and the oxygen source 18. Fitting 22 is coupled to the end of internal tubing 20 at the tail area 23 (although other locations are appropriate). Fitting 22 is inserted into main tubing 19 prior to handing the plaything to the patient. In the illustrated embodiment, the bear's tail covers the fitting 22.

Referring again to FIG. 2a, the internal tubing 20 is connected to at least one and, preferably, multiple oxygen outlet ports 24. The branches of tubing can be accomplished by using any desired combination of tubing connectors, such as cross connectors, "Y" connectors and "T" connectors. The oxygen ports can be as simple as the open ends of the tubing 20 or, preferably, diffusers which produce a larger area around the port to be saturated with oxygen. Diffusers could be molded from plastic in a desired shape with perforations formed in the plastic to allow the oxygen to exit. The oxygen ports can be exposed (i.e. visible on the external surface of the oxygenation device 16) or covered with material, so long as the oxygen can pass through the material.

The placement of the oxygen outlet ports 24 shown in FIG. 2a is designed to provide a nearly direct flow of oxygen to the patient's nose and mouth regions, regardless of the position the plaything is being held in by the patient. Because the goal is to have the patient hold the plaything near his or her face, it is desirable that oxygen be available in any position, such that the EMS personnel do not need to reorient the oxygenation device 16 while it is being held, which could be distracting or annoying to the patient and interfere with the calming presence of the oxygenation device 16.

Figure 2C:
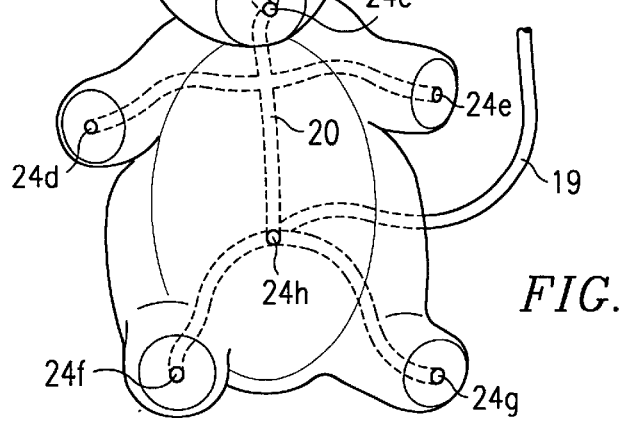
FIG. 2c illustrates a perspective view of the first embodiment of the pediatric oxygenation device using internal tube outlets for the oxygenation ports.

FIG. 2c illustrates an embodiment of the oxygenation device 16 using the free ends of the internal tubing as the oxygen outlet ports 24, rather than using diffusers as shown in FIG. 2a. In this embodiment, the free ends of the tubing (i.e., the ends of the tubing which are connected to the outlet ports in FIG. 2a) are exposed to the exterior of the oxygenation device 16 or behind a material which allows the oxygen to escape in the approximate area of the free ends.

Figure 3:
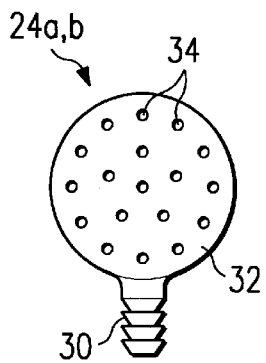

FIGS. 3 through 5a–b illustrate views of the oxygen ports 24 used in the bear of FIG. 2a. FIG. 3 illustrates an oxygen port which could be used for the bear's ear ports 24a–b. This oxygen port has a connector 30 for connecting to the internal tubing 20. The connector is coupled to ear piece 32 which has holes 34 formed on one side. The side of the ear piece 32 containing the holes 34 can be exposed to the exterior of the plaything or may be covered in cloth.

Figure 4A:
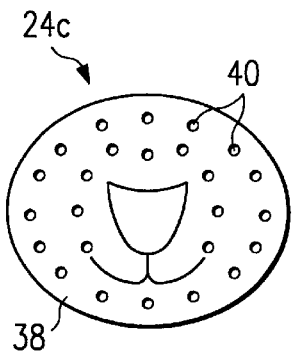
Figure 4B:
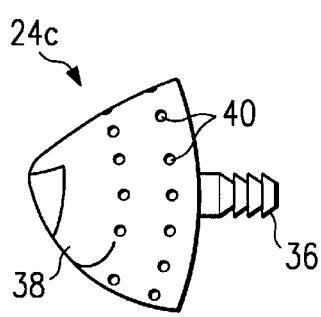

FIGS. 4a–b illustrate front and side views of an oxygen port which could be used for the bear's muzzle port 24c. This oxygen port also has a connector 36 for connecting to the internal tubing 20. The connector 36 is coupled to muzzle piece 38 which has holes 40 formed on the front cone-shaped portion.

Figure 5A:
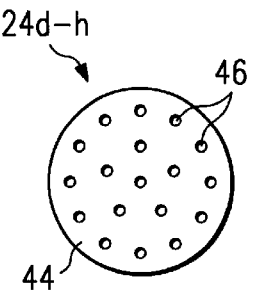
Figure 5B:
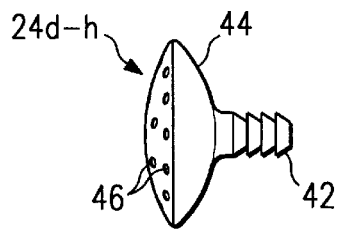

FIGS. 5a–b illustrate front and side views of an oxygen port which could be used for the bear's paw and belly ports 24d–h. This oxygen port has a connector 42 for connecting to the internal tubing 20. The connector is coupled to paw piece (or belly piece) 44 which has holes 46 formed on one side. The side of the paw or belly piece 44 containing the holes 46 can be exposed to the patient or may be covered in cloth.

Figure 6:
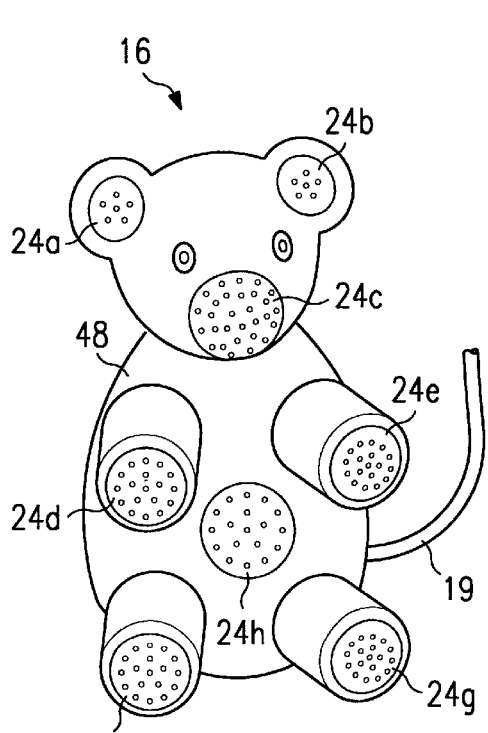
FIG. 6 illustrates an embodiment of a pediatric oxygenation device which does not use internal tubing.

FIG. 6 illustrates an embodiment of the oxygenation device 16 which does not need internal tubing. In this case a shell 48 receives the oxygen from the oxygen source 18 through main tubing 19. Oxygen is allowed to escape through oxygen ports 24 (individually referenced as oxygen ports 24a–h). The shell 48 could be made, for example, from a thin plastic material. Optionally, the shell 48 could be covered by a softer material, such as cloth, or colored, to make the plaything more interesting and inviting to a child.

The embodiment shown in FIG. 6 has an important advantage. By using a thin flexible material as the shell 48, the oxygenation device 16 can be made inflatable, which allows the oxygenation devices 16 to be stored in a smaller area. Upon receiving the oxygen from oxygen source 18, the device 16 will inflate to form the plaything, which can then be given to the child.

Emergency medical trucks, in particular, must carry a variety of devices for treatment of a large number of possible emergencies for both adults and children. Accordingly, space within an emergency medical vehicle is very valuable. By storing the oxygenation device 16 in a deflated state, a great deal of space may be preserved, since it is likely that each truck will carry multiple oxygenation devices.

Figure 7:
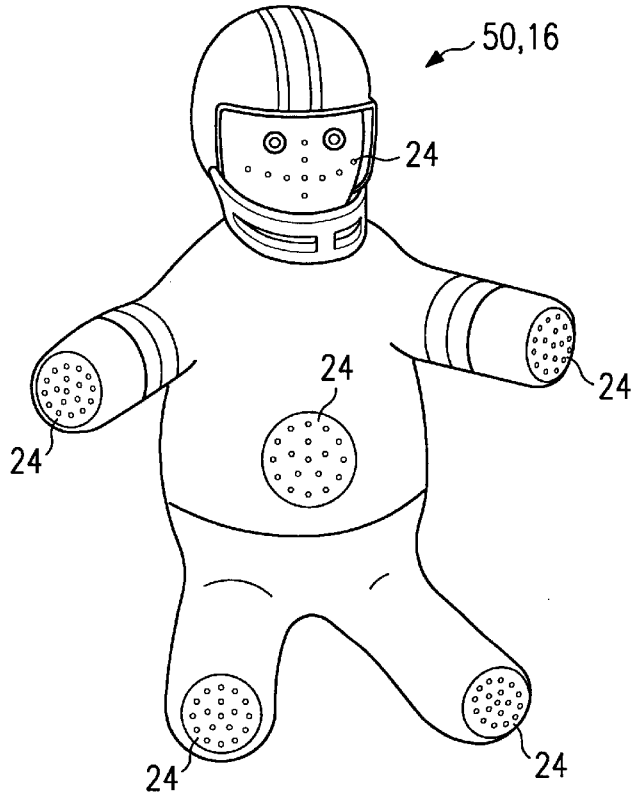
FIGS. 7–10 illustrate perspective views of alternative embodiments of the pediatric oxygenation device.

FIGS. 7–10 illustrate alternative embodiments for playthings 16 which would entice the patients to hold the plaything near their face. In FIG. 7, a football player doll 50 is shown having oxygen ports 24 on its face, hands, feet and belly areas. Similarly, other types of human dolls, such as Raggedy Anne and Raggedy Andy type dolls could be used with ports in the same general locations.

Figure 8:
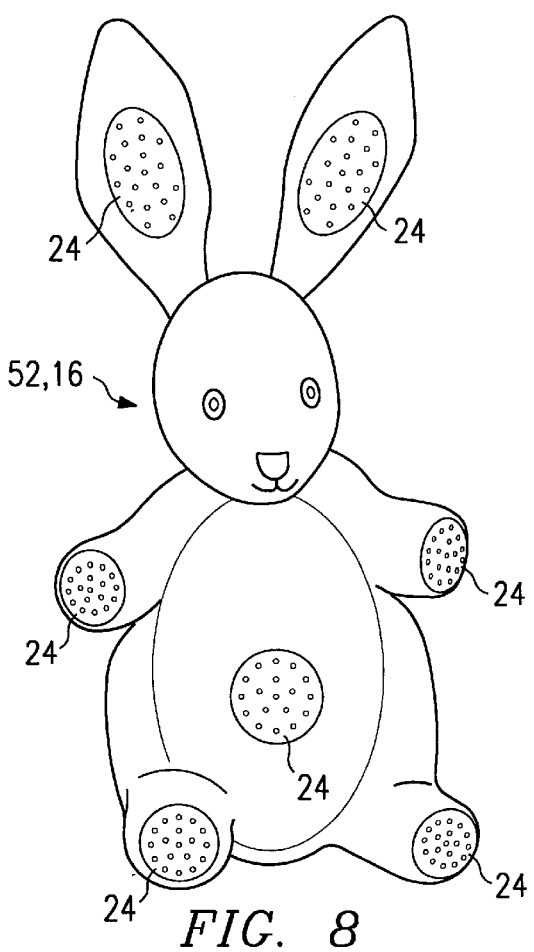

In FIG. 8, a bunny doll 52 is shown having oxygen ports 24 on its ears, paws and belly. Other animals figures which could be used are raccoons, dogs, cats, monkeys, dragons and dinosaurs to name a few.

Figure 9:
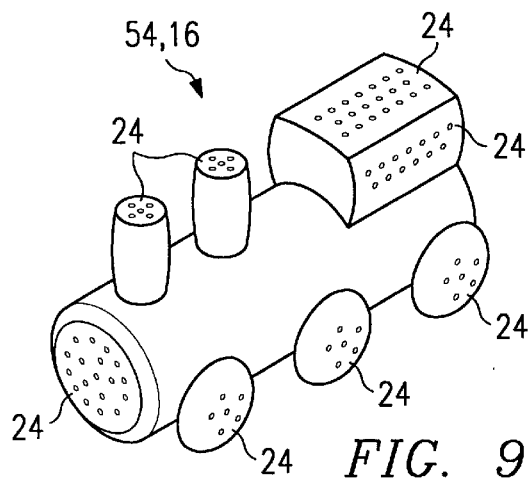

In FIG. 9, a train doll 54 is shown which has oxygen ports 24 on its front, smoke stacks, wheels and cabin. The train doll 54 could also have human characteristics, such as a face, to make it friendlier to small children.

Figure 10:
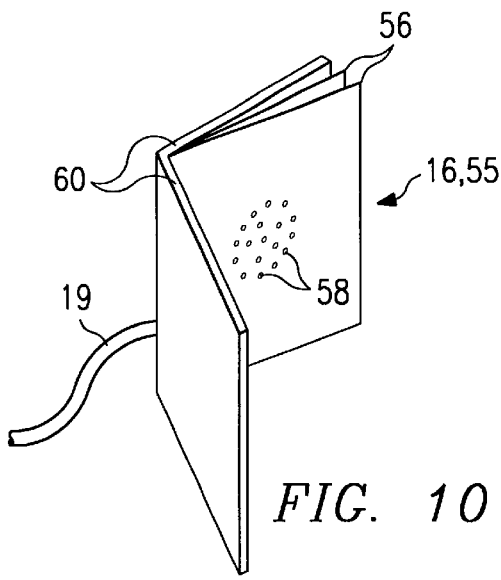

FIG. 10 illustrates a book 55 in which the oxygen may escape through the pages. Each page 56 could have holes 58 which correspond to holes in hollow cover pages 60. The cover pages would receive oxygen from the oxygen source 18 through main tubing 19. The child could flip pages to look at pictures while oxygen is directed toward the child's face. Multiple outlets would allow the book to be held in various orientations without impeding flow to the child's face.

Any number of plaything designs could be used in connection with the oxygenation device 16. Cars, telephones, and so on could be designed similar to the devices described above. Geometric playthings, such as spheres and cubes with interesting designs could also be used. Such geometric playthings are especially suited to an inflatable embodiment.

It may be desirable to have a number of different designs for the oxygenation device 16 available in the EMS setting, so that a child has a choice of a toy most suited to his or her liking. Some children may be especially attracted to animals, for example, while others are attracted to baby dolls. Since the oxygenation device 16 can be connected to an oxygen source in an extremely short period of time, giving the child a choice will not normally affect the oxygenation process.

Figure 11A:
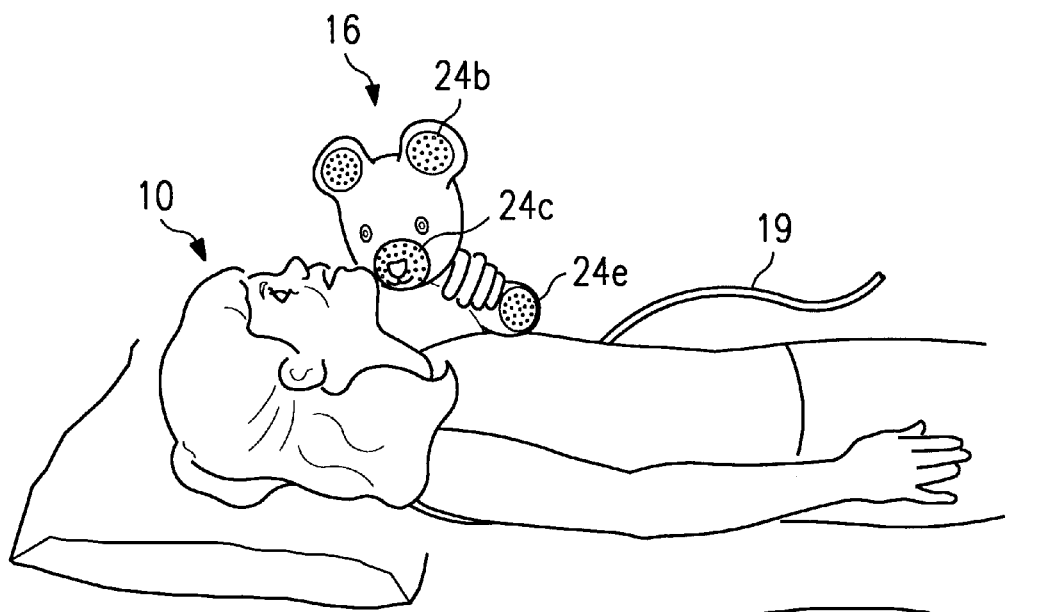
FIGS. 11a–d illustrate the oxygenation device of FIG. 2a in various orientations relative to the user's face.
Figure 11B:
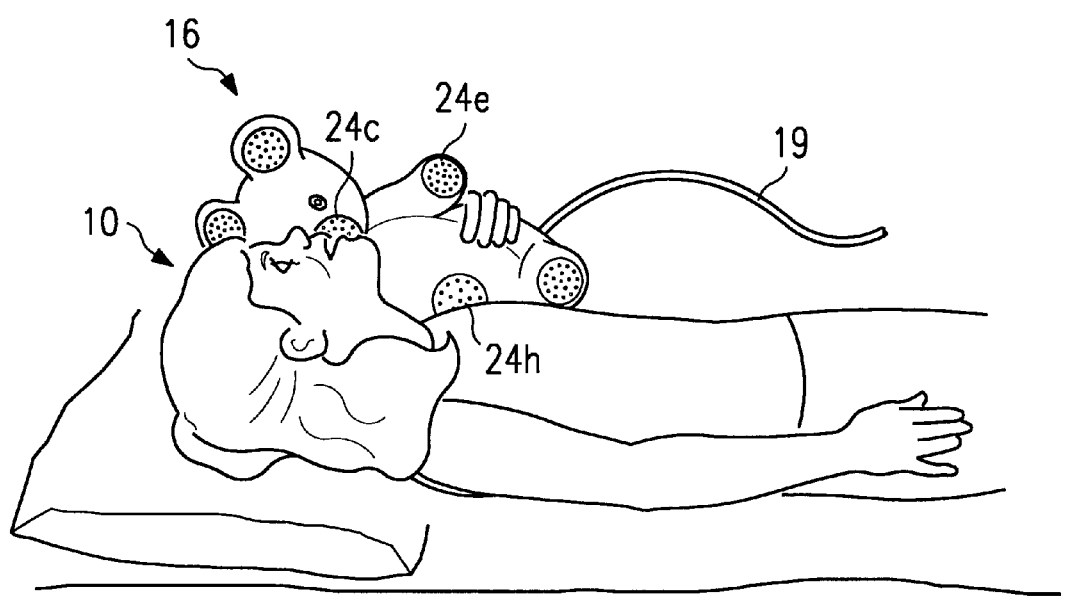

FIGS. 11a–d illustrate a patient 10 holding the oxygenation device 16 of FIG. 2a in a number of positions. As can be seen, no matter how the oxygenation device 16 is held, at least one oxygen port is disposed near the child's mouth and nose to maximize efficiency in oxygenation of the patient. In FIG. 11a, the oxygenation device 16 is held to the side of the patient with the nose of the bear proximate to the chin of the patient. In this configuration, the patient is receiving oxygen directly from the muzzle port 24c and the ear ports 24b. In FIG. 11b, the bear is held higher up to the side of the patient's head, such that the bear's arm is placed near the patient's chin. In this configuration the patient receives oxygen directly from the bear's muzzle port 24c, arm port 24e and belly port 24h.

Figure 11C:
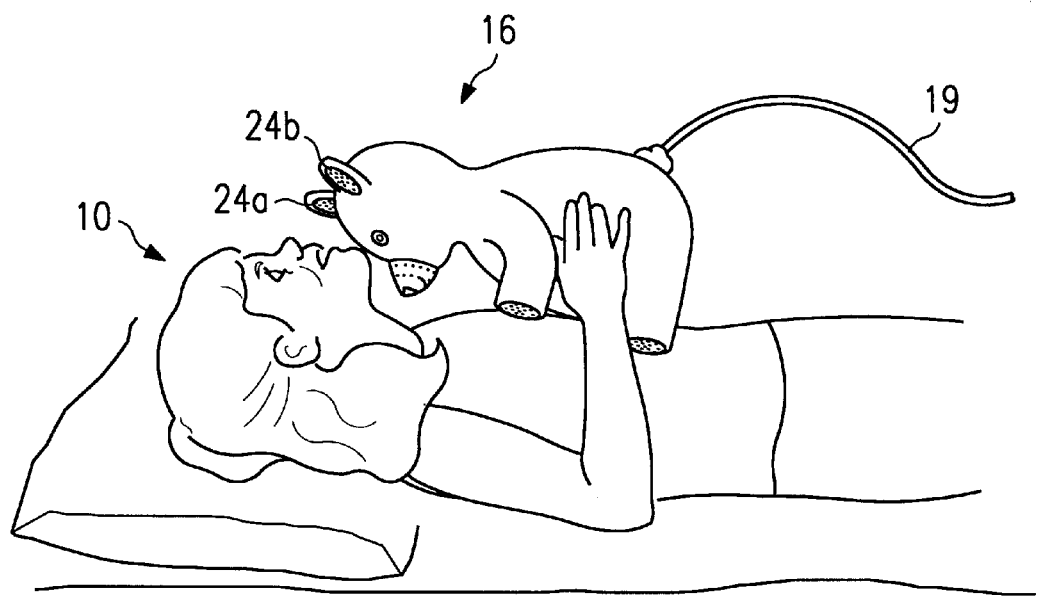
Figure 11D:
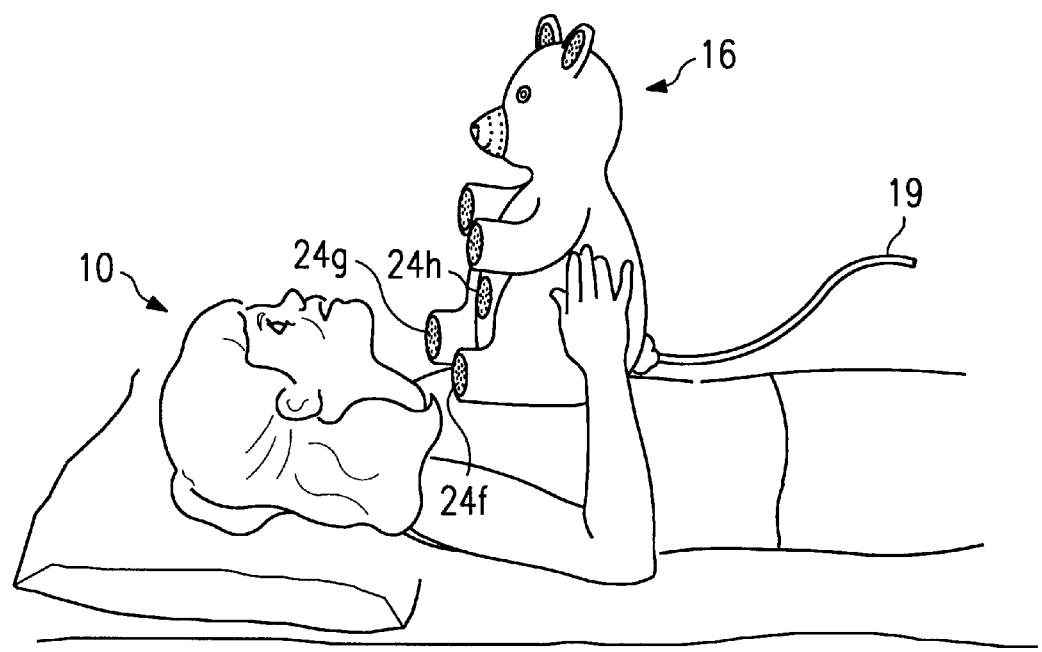

In FIG. 11c, the bear is held on top of the patient's chest, with the nose of the bear below the chin of the patient. In this orientation, the patient receives oxygen from the bears ear ports 24a–b and muzzle port 24c. In FIG. 11d, the bear is sitting on the patient's chest. In this orientation, the patient receives oxygen through the paws ports 24f–g and belly port 24h of the oxygenation device 16.

While the embodiments shown above use multiple ports for dispersing oxygen from different respective areas of the oxygenation device 16, a single integral outlet with multiple holes could extend across various areas of the oxygenation device to achieve the same result.

Figure 12:
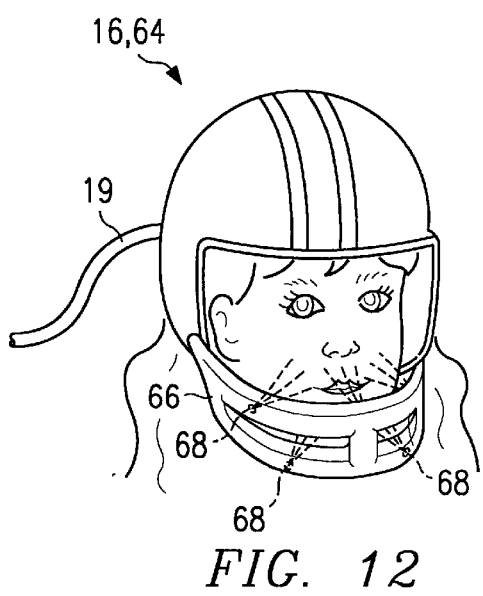
FIGS. 12 and 13 illustrate pediatric oxygenation device which can be worn by patient to emit oxygen in the nose and mouth areas of the child.
Figure 13:
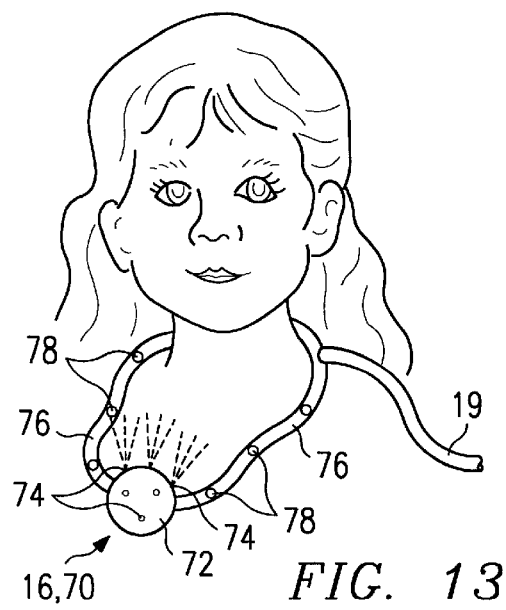

FIGS. 12 and 13 illustrate embodiments of oxygenation devices wherein the device is worn by the patient. In FIG. 12, a helmet 64 has a mouth guard or face mask 66 with one or more oxygen ports 68 directed towards the child's nose and mouth areas. The tubing 19 could be connected to the face mask 66. In the preferred embodiment, other oxygen ports 68 would be disposed around the helmet so that a child who wished to hold the helmet, rather than wear the helmet, would still have oxygen directed to his or her face. Typically, the helmet would be made of a soft material or plastic, as opposed to a hard shell helmet. Optionally, the helmet 64 could be made inflatable.

Similarly, in FIG. 13, a necklace 70 has a pendant 72 with one or more outlets 74 directed towards the patient's nose and mouth areas. The main tubing 19 is connected to the tubing 76 which is connected to the pendant 72. The tubing 76 can also have holes 78 to outlet oxygen towards the sides of the patient's face. Preferably, the necklace 70 has outlets 74 directed in multiple directions such that it could be either worn around the child's neck or held. The pendant 72 could be made of hard or soft materials, or could be inflatable.

Other designs for playthings which could be worn by the child would include, for example, oversized glasses or sunglasses.

The present invention provides significant advantages over the prior art. First, it delivers oxygen to a pediatric patient without adding to stress. Second, it may actually reduce stress in the patient. Third, it can deliver oxygen over a wide area, allowing the patient to interact with the plaything in a natural manner while maintaining a direct flow of oxygen to the patient's mouth and nose regions. Fourth, the oxygenation device can be inexpensively made. Fifth, different designs can be used to appeal to a wide range of pediatric patients.

While the oxygenation device is specifically designed for use with pediatric patients, it should be noted that it can be used with older children and adults as well to provide areas of super-saturated oxygen when the patient refuses a mask. Also, while the oxygenation device is described herein as providing oxygen to the patient, other gases could also be used in connection with the device.

Although the Detailed Description of the invention has been directed to certain exemplary embodiments, various modifications of these embodiments, as well as alternative embodiments, will be suggested to those skilled in the art. The invention encompasses any modifications or alternative embodiments that fall within the scope of the Claims.

What is claimed is:

1. A method of supplying gas to a pediatric patient, comprising the steps of:

supplying the patient with a plaything-shaped receptacle to be held in the general direction of the patient's face region without attachment to the patient's face region, so that the patient may face the plaything-shaped receptacle;

dispersing gas through at least one port in said receptacle to produce a wide area of high gas concentration in front of the patient's mouth and nose regions independent of the orientation and position of the receptacle, as it is held in front of the patient's face.

2. The method of claim 1 wherein said dispersing step comprises the step of dispersing gas through a plurality of outlet ports disposed in the plaything, such that multiple areas of high oxygen concentration are produced.

3. The method of claim 2 wherein said step of dispersing gas comprises the step of providing gas from an gas tank through a tube coupled to said plaything.

* * * * *